(12) United States Patent
Horton et al.

(10) Patent No.: US 10,517,902 B2
(45) Date of Patent: Dec. 31, 2019

(54) EXPANDABLE AMNION MEMBRANE FOR TREATING NON-HEALING WOUNDS

(71) Applicant: PRIME MERGER SUB, LLC, Birmingham, AL (US)

(72) Inventors: Kenneth L. Horton, Birmingham, AL (US); Gregory J. Yager, Mount Olive, AL (US); Howard P. Walthall, Jr., Birmingham, AL (US)

(73) Assignee: Prime Merger Sub, LLC, Birmingham, AL (US)

( * ) Notice: Subject to any disclaimer, the term of this patent is extended or adjusted under 35 U.S.C. 154(b) by 0 days.

(21) Appl. No.: 13/826,139

(22) Filed: Mar. 14, 2013

(65) Prior Publication Data
US 2015/0216910 A1  Aug. 6, 2015

Related U.S. Application Data

(63) Continuation-in-part of application No. 13/647,525, filed on Oct. 9, 2012, now abandoned, and a continuation-in-part of application No. 13/250,096, filed on Sep. 30, 2011, now abandoned.

(51) Int. Cl.
| | | |
|---|---|---|
| A61K 35/50 | (2015.01) | |
| A61L 27/36 | (2006.01) | |
| C12N 5/073 | (2010.01) | |
| A61L 15/40 | (2006.01) | |

(52) U.S. Cl.
CPC .............. *A61K 35/50* (2013.01); *A61L 15/40* (2013.01); *A61L 27/3604* (2013.01); *C12N 5/0605* (2013.01)

(58) Field of Classification Search
CPC ............................ A61K 38/00; A61K 39/3855
USPC ............................................. 424/134.1, 192.1
See application file for complete search history.

(56) References Cited

U.S. PATENT DOCUMENTS

| 10,105,398 | B2 * | 10/2018 | Morse .................... A61K 35/50 |
| 2004/0048796 | A1 * | 3/2004 | Hariri .................... A61K 35/50 424/423 |
| 2005/0021141 | A1 * | 1/2005 | Bleyer .................... A61L 15/40 623/15.12 |
| 2005/0107876 | A1 * | 5/2005 | Kim et al. ................. 623/15.12 |
| 2005/0147656 | A1 * | 7/2005 | McCarthy ......... A61F 13/00034 424/445 |
| 2007/0042024 | A1 * | 2/2007 | Gladman ............ A61F 13/0273 424/445 |
| 2007/0231297 | A1 * | 10/2007 | Smith .................... A61K 35/50 424/85.1 |
| 2008/0046095 | A1 * | 2/2008 | Daniel ................ A61L 27/3604 623/23.74 |
| 2010/0104539 | A1 * | 4/2010 | Daniel ................ A61L 27/3604 424/93.7 |

FOREIGN PATENT DOCUMENTS

WO    WO 09/052132    *   4/2009    ............. A61K 35/50

OTHER PUBLICATIONS

Barry et al. (The International Journal of Biochemistry and Cell Biology, vol. 36, p. 568-584, 2004.*
Fliniaux et al. (Differentiation, vol. 72, p. 558-565, 2004).*
Ganatra et al. (Journal of Pakistan Medical Association, vol. 53, No. 1, p. 1-7, 2003).*
Wu et al. (Stem Cells, vol. 25, No. 10, p. 2648-2659, 2007).*
"Anatomy and Pathology of the Placental Membranes." Pathology of the Human Placenta. Ed. K Bernirschke, P Kaufmann, R Baergen. New York: Springer, 2006. pp. 321-379. Print.*
"Stem Cell." Merriam-Webster.com. Merriam-Webster, n.d. Web. Sep. 22, 2016. <http://www.merriam-webster.com/dictionary/stem%20cell.*
Douglas, "Homografts of fetal membranes as coverings for wounds" The Journal of the Tennessee State Medical Association, 1952, vol. 45, No. 6, pp. 230-235. (Year: 1952).*
Mesh. (n.d.). Retrieved Mar. 8, 2018, from https://www.merriam-webster.com/dictionary/mesh (Year: 2018).*
Fletcher, Jacqui, "Dressing: Cutting and application guide" World Wide Wounds, 2007, 10 pages. (Year: 2007).*
Yoon et al, Stem Cells and Development, 2010, vol. 19 No. 6, pp. 887-902. (Year: 2010).*

* cited by examiner

*Primary Examiner* — Allison M Fox
(74) *Attorney, Agent, or Firm* — C. Brandon Browning; Maynard, Cooper & Gale, PC

(57) ABSTRACT

The present disclosure generally pertains to methods of treating non-healing wounds. Specifically, the method includes injecting amnion fluid derived cells along the periphery of the wound. The wound is then treated with a placental membrane material including a plurality of slits for increasing the membranes capacity to expand. The slits produce a mesh-like pattern in the membrane material. The amniotic derived cells deliver to the wound electrolytes, growth factors, carbohydrates, lipids, proteins, amino acids, lactate, pyruvate, enzymes, hormones and other factors useful in wound repair. The membrane material provides a scaffolding structure supporting cell growth, prevents microbial infection and decreases the rate of passive evaporative water and heat loss. The combination of the amniotic derived cells and the membrane material protects the wound and promotes cell regeneration.

17 Claims, 6 Drawing Sheets

EXPANDABLE AMNION MEMBRANE FOR TREATING NON-HEALING WOUNDS

RELATED REFERENCES

This application claims priority to U.S. patent application Ser. No. 13/250,096, filed on Sep. 30, 2011, and titled, "Expandable Placental Membrane and Methods of Making and Storing Same" and U.S. patent application Ser. No. 13/647,525, filed on Oct. 9, 2012, and titled, "Expandable Placental Membrane and Methods of Making and Storing Same," the entire contents of which are incorporated herein by reference.

FIELD OF THE INVENTION

The present invention is directed to a method of treating non-healing wounds. More particularly, the present invention is directed to a method utilizing amniotic derived cells and an expandable placental membrane for treating non-healing wounds and burns.

BACKGROUND OF THE INVENTION

Wound healing is a complex process where the skin or another organ or tissue repairs itself after injury. In normal skin, the epidermis (outermost layer) and dermis (inner or deeper layer) form a protective barrier against the external environment. If the protective barrier is broken, the normal process of wound healing is immediately set in motion. Upon injury to the skin, a set of complex biochemical events takes place to repair the damage. The classic model of wound healing is divided into several sequential, yet overlapping phases. Effective wound healing requires the highly organized integration of complex molecular and biological events including cell proliferation, migration and extracellular matrix (ECM) deposition. The speed of wound healing can be impacted by many factors, including the health of the individual and the bloodstream levels of certain hormones.

The wound healing process is not only complex but fragile, and susceptible to interruption or failure leading to the formation of non-healing chronic wounds. A non-healing wound is one that fails to heal with standard therapy in an orderly and timely manner (Troxler, M. et al., "Integrating adjunctive therapy into practice: the importance of recognizing 'hard-to-heal' wounds." World Wide Wounds 2006. Available from http://www.worldwidewounds.com/2006/december/Troxler/Integrating-Adjunct-Therapy-Into-Practice.html). One of the major factors responsible for the appearance of chronic wounds is the impairment of cytokine release by local fibroblasts and inflammatory cells, which can result in reduced angiogenesis (Falange, V. (2005) "Wound healing and its impairment in the diabetic foot," Lancet 366: 2736-1743). Many health-related factors may contribute to the development of non-healing wounds, including immunological diseases, diabetes, venous or arterial disease, advanced age, and infection.

Healing may be promoted by restoring or preventing the breakdown of the skin or tissue/organ extracellular matrix. This may be accomplished through the addition of deficient components, such as growth factors or collagen, or the introduction of a temporary matrix to support the growth of new cells or tissue. Regenerative therapies involve the use of living cells to repair, replace or restore normal function to damaged tissues and organs. Stem cells are viewed as a promising candidate for use in cell-based wound healing therapies due to their capacity for self-renewal and differentiation. Both adult and embryonic stem cells are commonly used to develop therapies for various models of disease and injury. However, a number of limitations hamper the clinical applicability of stem cells derived from adults or developing embryos, such ethical concerns and limitations on the cell sample size.

Subpopulations of stem cells exist in both the amniotic membrane and the amniotic fluid. Amniotic fluid cells are obtained during amniocentesis or scheduled C-section while amniotic membrane cells are obtained from the amnion membrane which is discarded after birth. These cells are therefore readily available, easily procured and avoid the ethical issues surrounding the use of embryonic stem cells.

Human amniotic fluid is a dynamic environment, which undergoes multiple developmental changes in order to sustain fetal growth. Fluid secretions from the fetus into the amniotic fluid carry a variety of fetal cells, resulting in a heterogeneous population of cells derived from fetal skin, gastrointestinal, respiratory and urinary tracts, and the amniotic membrane. These cells express electrolytes, growth factors, carbohydrates, lipids, proteins, amino acids, lactate, pyruvate, enzymes, hormones and other factors useful in tissue repair. Because they are readily accessible and pose little to no ethical concerns, amniotic fluid-derived cells are a promising alternative source of cells for use a strategy for cell replacement in various injury models. U.S. Patent Application Publication No. 2010/0130415 (Cohen et al.) describes formulations comprising secreted products obtained from the culture medium of stem cells, such as umbilical cord blood stem cells, for enhancement of wound healing.

Human amniotic membrane is the innermost fetal layer, lining the amniotic cavity and protecting the fetus during pregnancy. The membrane is composed of an inner amnion layer facing the fetus and a generally inelastic outer shell or chorion. Clinicians have used intact placental membrane composed of an amnion and a chorion layer in medical procedures since as early as 1910 (Davis, J. S., "Skin Transplantation with a Review of 550 Cases at the Johns Hopkins Hospital," *John Hopkins Med. J.*, 15:307 (1910)). As an alternative to intact placental membrane, some clinicians separate the amnion from the placental membrane, using only the amnion layer.

Certain characteristics of the placental membrane make it attractive for use by the medical community. The placental membrane has a wide number of applications in regenerative medicine, including providing scaffolding or structure for the regrowth of cells and tissue. An important advantage of placental membrane in scaffolding is that the amnion contains an epithelial layer. The epithelial cells derived from this layer are similar to stem cells, allowing the cells to differentiate into cells of the type that surrounds them. Additional cells similar to stem cells are contained in the body of the membrane, and the membrane also contains various growth and trophic factors, such as epidermal, insulin-like and fibroblast growth factors, and high concentrations of hyaluronic acid which may be beneficial in preventing scarring and inflammation and supporting healing. Thus, placental membrane offers a wide-variety of advantages for medical uses.

Although placental membranes possess many benefits and applications, availability of the membranes has limited their use. The amount of placental membrane generated from a single birth is small. As would be expected, because the supply of placental membranes is relatively small, the cost of placental membranes limits their use only to procedures that surpass a certain price or complexity. U.S. patent application Ser. Nos. 13/250,096 and 13/647,525, describe a placental membrane including a plurality of slits for increasing the membranes capacity to expand. The slits are provided through the membrane and are provided in sufficient numbers to produce a mesh-like pattern which enables the membrane to be stretched and therefore increase its length and width.

Many conditions would benefit from the application of a lattice or support system in conjunction with hormones and growth factors to treat non-healing wounds and burns. Accordingly, there is need for methods of treating wounds which utilize placental membranes in conjunction with cells derived from human amniotic fluid.

SUMMARY OF THE INVENTION

The present invention is directed to methods of treating non-healing wounds and burns. According to one aspect of the invention, the method includes injecting amnion fluid derived cells along the periphery of the wound. The cells are isolated from amniotic fluid from human donors. In an additional aspect, the cells are isolated from a donor amniotic membrane. The amniotic derived cells deliver a number of beneficial biological substance to the wound site which are useful in wound repair.

The wound is then treated with an expandable placental membrane material including a plurality of slits for increasing the membrane's capacity to expand, thereby covering a larger wound surface using less amniotic material. The slits produce a mesh-like pattern in the membrane material that covers the entire upper and lower surfaces of the membrane. The membrane material provides a scaffolding structure supporting cell growth, prevents microbial infection and decreases the rate of passive evaporative water and heat loss. The combination of the amniotic derived cells and the membrane material protects the wound and promotes cell regeneration. Alternatively, the wound may be treated by placement of expandable placental membrane material without concurrent injection of cells. The treatment of non-healing wounds with amniotic derived cells and an amniotic membrane material generates an environment that both protects the wound from further damage and infection and provides support and nutrients to accelerate wound healing.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Figure 1:
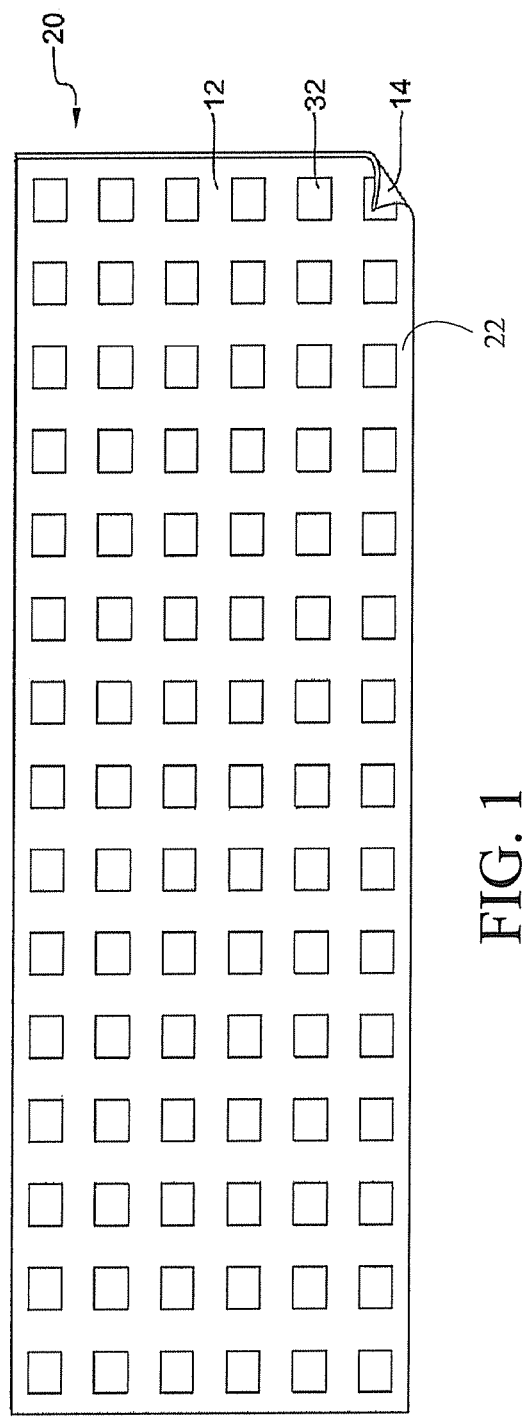
FIG. 1 is a top plan view of an expanded placental membrane in accordance with the present invention.

FIG. 1 depicts an expandable, porous placental membrane material 20 that is prepared from a placental membrane as described in U.S. patent application Ser. Nos. 13/250,096 and 13/647,525, the contents of which are herein incorporated by reference in their entirety. Placental membrane material 20 is processed in a manner that allows it to exhibit expansion ratios of up to 6:1 or more including 2:1, 3:1, 4:1 and 5:1, thereby allowing the material to cover up to six times the treatment area than the original placental membrane. This is accomplished by forming a plurality of openings through the original placental membrane and imparting to the membrane a mesh-like pattern. The resulting expandable, porous placental membrane material 20 enables material 20 to stretch along its length and width thereby increasing the perimeter of material 20 and the amount of surface area it can cover when placed on or in a wound, burn or the like.

Referring again to FIG. 1, placental membrane material 20 includes a plurality of elongated slits 22 which in combination provide material 20 with a mesh-like appearance. Slits 22 extend between and through amnion layer 12 and chorion layer 14 and are formed by processing the original placental membrane with a mesher, for example, as described in U.S. Pat. Nos. 6,063,094; 5,004,468; 3,640,279; 3,472,228 and 3,358,688. Depending on the mesher settings, and more particularly, the arrangement and number of the cutting portions of the mesher, slits 22 can vary in size, density and orientation. By varying slit 22 sizes, densities and orientation the capacity for placental membrane material 20 to expand can be controlled. The mesh pattern may be rectangular shaped 32 as seen in FIG. 1 or hexagonal shape (not pictured). Alternatively, it is anticipated that the openings formed through placental membrane material can be shaped other than as slit 22, and thus the mesh-like pattern may include shapes other than squares. Alternatively, the amnion and chorion may be separated and either the amnion or the chorion alone may be used.

In addition to increasing the capacity for material 20 to expand and cover a larger wound area, formation of slits 22 in the material imparts a porosity to the original placental material that is not found in the membrane by virtue of the impermeable nature of the intact placental membrane. By providing pathways through material 20, wound draining is facilitated and movement of molecules and cells across placental membrane material 20 enabled. These properties are expected to increase the effectiveness of material 20 in certain wound healing and grafting applications.

Preferably, slits 22 are dispersed over the entire surface of material 20 in order to maximize expandability of the material; however, is anticipated that there may be applications where expandability or porosity of material 20 may be desired for only certain portions of the material. In those instances, slits 22 may be provided in only a fraction of the material or limited only to certain areas of the material such as around the perimeter of the material, in a central portion of the material, or within a top, bottom, left or right half of the material.

In practice, the amniotic membrane is harvested from consenting seronegative (hepatitis B and C virus, syphilis and human immunodeficiency virus) maternal donors during vaginal, emergency and elective caesarian section deliveries. Under sterile conditions, the placental membrane is washed to remove clots and debris. The membrane may also be incubated in a cocktail of antimicrobial medium to prevent infection. The membrane is then treated to expand the membrane and stored until use, as described in U.S. patent application Ser. Nos. 13/250,096 and 13/647,525.

Figure 2:
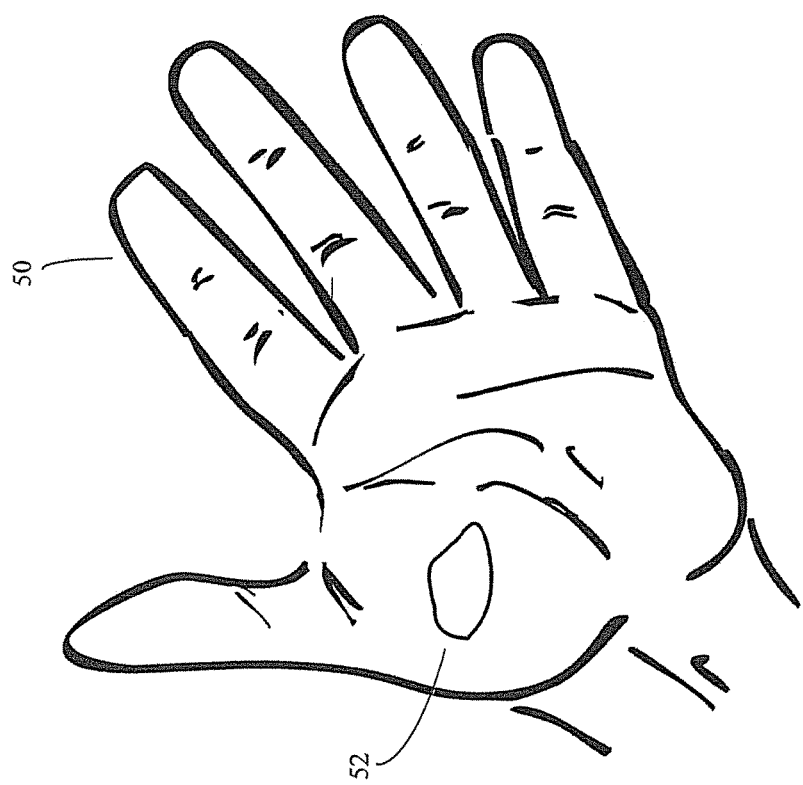
FIG. 2 is a top plan view of a non-healing wound located on the hand.

FIG. 2 depicts a patient member 50 exhibiting a non-healing wound 52. The member 50 illustrated in FIG. 2 represents a hand. However, the methods of the present invention are applicable to wounds located on other portions of the body, for instance the feet, arms, legs, back, abdominal area, etc. The non-healing nature of wound 52 is classified and diagnosed by a medical professional following established guidelines as are known to one of skill in the art. Wound 52 may be caused by a number of factors, for example a compromised immunological system, trauma such as laceration or burn, or an underlying medical condition. The methods of the present invention are not limited to a particular type of non-healing wound or a specific medical condition.

Figure 3:
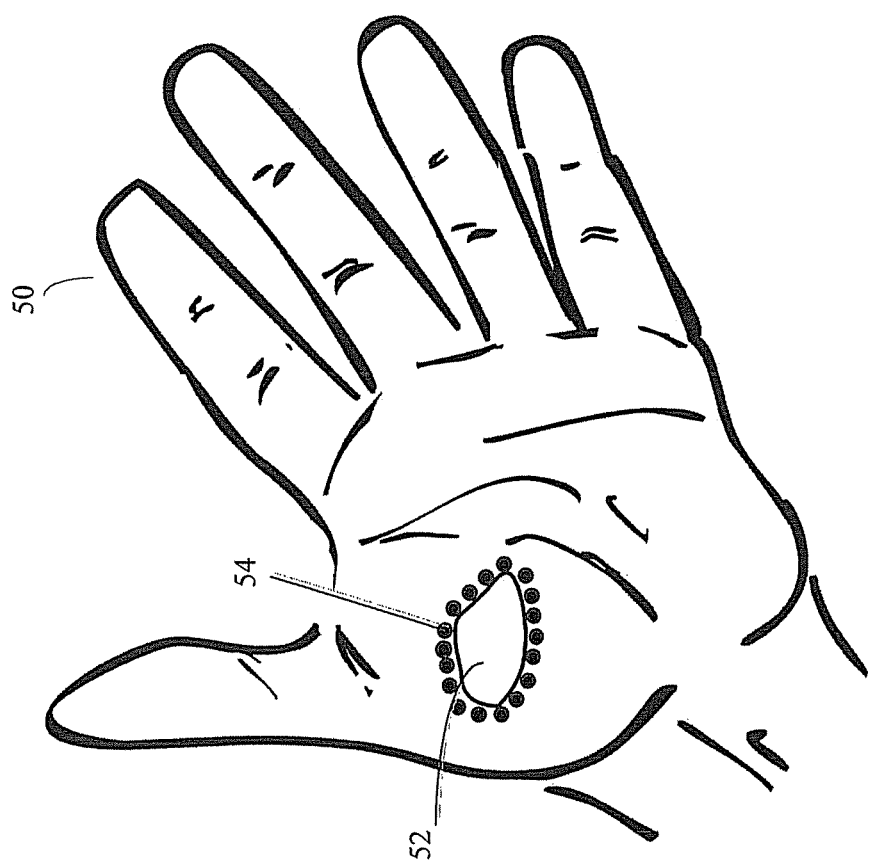
FIG. 3 is a top plan view of a non-healing wound with a plurality of amniotic derived cell injection sites.

FIG. 3 illustrates the first step one embodiment of the method of the invention. Here, member 50 is again illustrated as including non-healing wound 52. FIG. 3 further illustrates a plurality of injection sites 54 located along the periphery of non-healing wound 52. The present invention is not limited to the number and placement of injection sites 54 illustrates in FIGS. 4-6, as the quantity and location may change. In one embodiment, injection sites 54 indicate the location where amniotic derived cells are injected to aid in wound healing. The number and volume of cells injected may vary as is known to one of skill in the art. For example, $1 \times 10^6$ cells suspended in 100 ul of fluid may be are injected intra-dermally at injection sites 54 around the non-healing wound 52.

In one embodiment, the cells injected at injection sites 54 cells are isolated from amniotic fluid from human donors, collected for instance via amniocentesis, or more preferably at elective c-section. The cells may also be purified from or extracted from the amnion 12 or chorion 14 layer of the amniotic membrane. In this embodiment, the tissue is disrupted using techniques known in the art, for instance through homogenization. The cells may be further purified utilizing enzymatic and mechanical methods as known in the art. The cells may or may not be cultured, and may be cryopreserved for storage. The cells isolated utilizing the above described method are herein referred to collectively as "amniotic derived cells".

The amniotic derived cells may be suspended an isotonic solution that will not cause any adverse physical or immunological effects. One example of an isotonic solution is saline, or phosphate buffered saline (PBS). The amniotic derived cells are best utilized with a previously cleaned and debrided wound to prevent infection. In a preferred embodiment, the cells are injected intra-dermally at the specified location(s) 54. The cells may be introduced at the wound site 54 immediately after isolation. In an additional embodiment, previously cryopreserved cells, isolated from either amniotic fluid or amniotic membrane, may be reconstituted by methods known in the art, and suspended in an isotonic solution before injection at the periphery of the wound site 54. The cells may be cryopreserved with expanded amniotic membrane from the same donor. Cryopreserved amniotic membrane retains the histological and morphological properties of fresh tissue. The amniotic derived cells express electrolytes, growth factors, carbohydrates, lipids, proteins, amino acids, lactate, pyruvate, enzymes, hormones and other factors useful in wound repair. These cells may also accelerate wound closure, increase re-epithelialization and increase cellularity, thus promoting wound healing.

Figure 4:
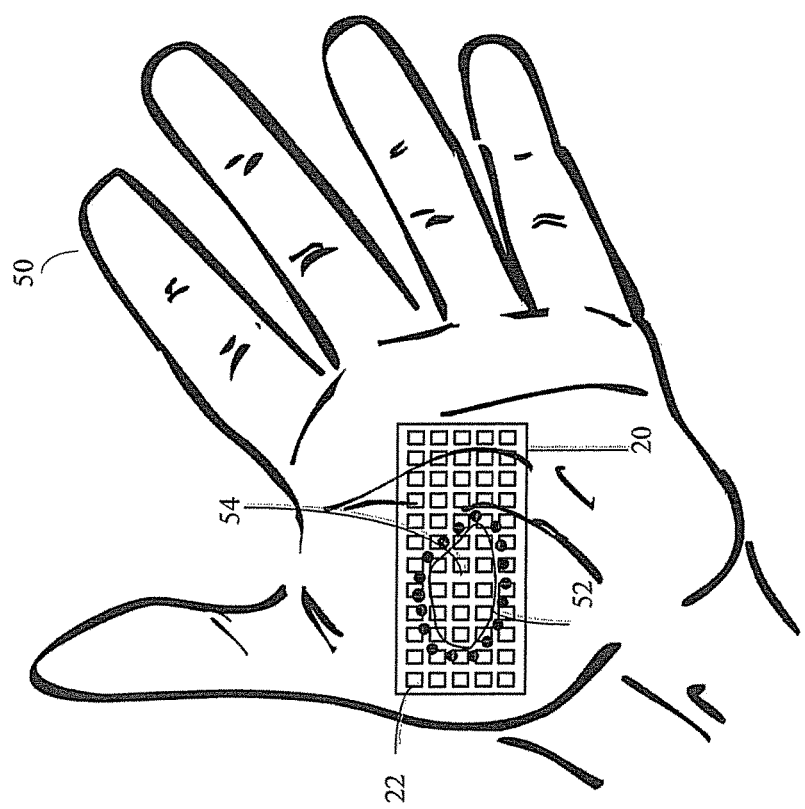
FIG. 4 is a top plan view of a non-healing wound with a plurality of amniotic derived cell injection sites and a membrane material overlapping the wound.

FIG. 4 depicts an additional step in one embodiment of the method of the invention. Here, a porous placental membrane material 20 is applied to the top of a non-healing wound 52 which has been treated with intra-dermal injections 54 of amniotic derived cells, as described above. In a preferred embodiment, the application of the membrane material 20 occurs concurrently with, or as soon as possible after, the injection of the amniotic derived cells. The amniotic membrane consists of a single layer of cuboidal epithelial cells, a thick basement membrane and an avascular stromal matrix, loosely attached to the chorion. The membrane material 20 is applied evenly with the stromal side in contact with the area of the wound 52 previously cleaned and debrided. By means of the slits provided within it, the membrane may be expanded to appropriately cover the wound surface. Air and fluid blebs are smoothed out to ensure total contact with the wound 52. The membrane material 20 is then trimmed to the appropriate width and size (not shown in FIGS. 4-6). A dressing may be applied to cover the membrane material 20, but its use is not necessary.

The amniotic membrane material 20, acting in conjunction with the injected amniotic derived cells, serves to enhance regeneration and healing of wounds. As stated above, the cells provide hormones, enzymes, growth factors and other molecules useful in wound repair. The membrane material 20 is utilized in wound regeneration because of its ability to provide structure supporting cell growth, diminish the occurrence of adhesions and scarring, enhance epithelialisation, and provide antimicrobial potential. In addition, use of a membrane 20 decreases the rate of passive evaporative water and heat loss.

Figure 5:
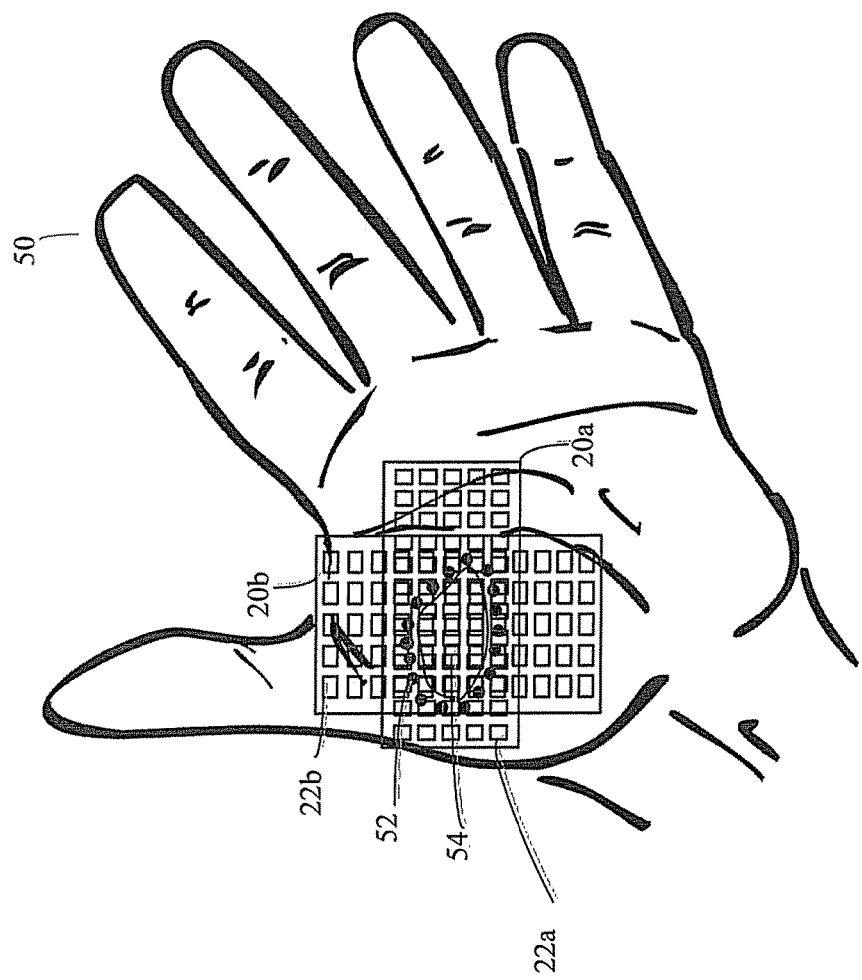
FIG. 5 is a top plan view of a non-healing wound with a plurality of amniotic derived cell injection sites and a plurality of membrane materials overlapping the wound in a lattice configuration.
Figure 6:
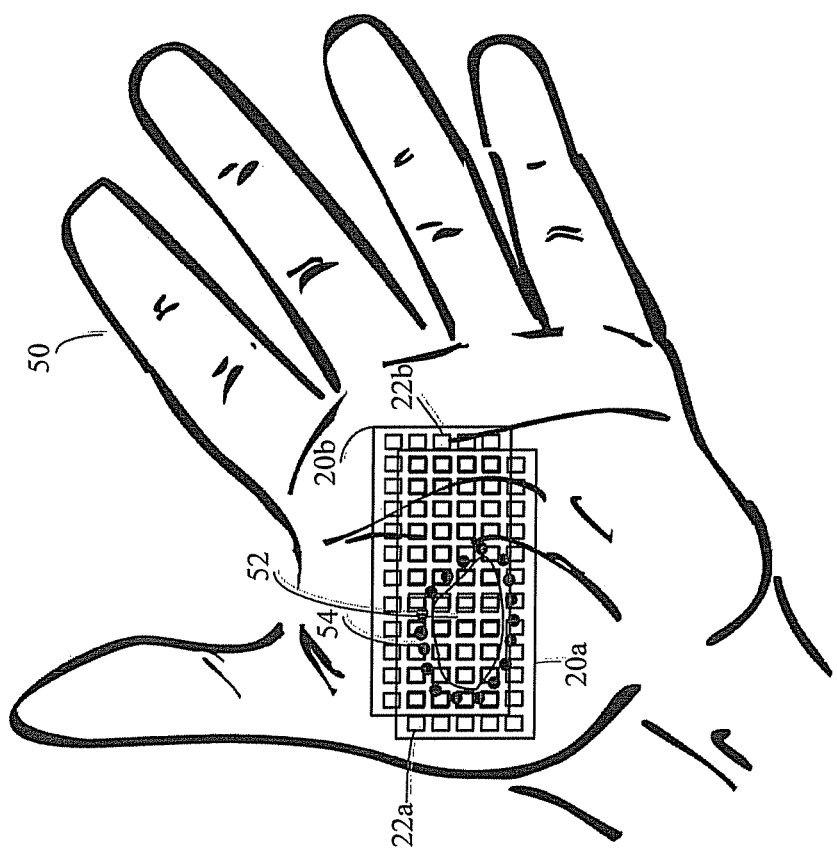
FIG. 6 is a top plan view of a non-healing wound with a plurality of amniotic derived cell injection sites and a plurality of membrane materials overlapping the wound in an overlapping configuration.

FIGS. 5 and 6 illustrate alternate embodiments of the invention utilizing a plurality of membrane materials 20. Here, two membrane materials 20a and 20b are applied evenly on the surface of wound 52. Although two membrane materials 20 are utilized in these illustrated embodiments, one of skill in the art will recognize that the use of other number of membranes 20 is also possible. Membrane material 20a is applied evenly with the stromal side in contact with the area of the previously cleaned and debrided wound 52. Air and fluid blebs are smoothed out to ensure total contact with the wound 52. The membrane material 20a is then trimmed to the appropriate width and size (not shown in FIG. 5). Membrane material 20b is then placed with the stromal side in contact with the epithelial side of membrane material 20a. Air and fluid blebs are smoothed out to ensure total contact with material 20a and excess material trimmed to insure full coverage of wound 52 (not shown). As illustrated in FIG. 5, the elongated slits 22a and 22b of overlapping membrane materials 20a and 20b have alternating orientations so that the rectangular shaped slits do not completely align. The membranes 20a and 20b form a lattice-type structure. The embodiment illustrated in FIG. 6 also utilizes two overlapping membrane materials 20a and 20b. Here, however, the elongated slits 22a and 22b are aligned so that the rectangular slits overlap. One of skill in the art will recognize that other orientations besides lattice and overlapping are possible. Multiple membranes 20 may afford protection to particularly large wounds which are not completely covered with a single membrane material 20 and also provide an additional impediment to bacterial contamination and reduce heat and moisture loss.

The concurrent treatment of non-healing wounds with a combination of amniotic derived cells and an amniotic membrane material generates an environment that both protects the wound from further damage and infection and provides support and nutrients to accelerate wound healing. The amniotic derived cells deliver to the wound growth factors, lipids, proteins, enzymes, hormones and other factors useful in wound repair. The membrane material provides a scaffolding structure supporting cell growth, prevents microbial infection and decreases the rate of passive evaporative water and heat loss. The combination of the amniotic derived cells and the membrane material protects the wound and promotes cell regeneration.

Now, therefore, the following is claimed:

1. A method for treating a wound comprising,
   forming a suspension including a plurality of amniotic fluid cells and a plurality of cells derived from amnion suspended in an isotonic solution, wherein the plurality of amniotic fluid cells and the plurality of cells derived from the amnion are not cultured cells,
   cryopreserving the suspension,
   reconstituting the suspension,
   injecting the reconstituted suspension intra-dermally at a plurality of locations about the periphery of the wound,
   applying a first placental membrane material to the wound, and
   applying a second placental membrane material to the first placental membrane material,
   wherein the first placental membrane material and second placental membrane material each includes an amnion layer and a chorion layer,
   wherein the first placental membrane material and the second placental membrane material partially overlap, and
   wherein the amnion layer includes a single layer of cuboidal epithelial cells, a basement membrane layer and a stromal layer.

2. The method according to claim 1 wherein the suspension includes fetal cells.

3. The method according to claim 1 further comprising contacting the stromal layer of the first placental membrane material directly to the wound.

4. The method according to claim 1 wherein a stromal-side of the second placental membrane material is applied to the single layer of cuboidal epithelial cells of the first placental membrane material.

5. A method of treating a wound comprising,
   forming a suspension including a plurality of amniotic fluid cells and a plurality of cells derived from amnion, wherein the plurality of amniotic fluid cells and the plurality of cells derived from the amnion are not cultured cells,
   cryopreserving the suspension,
   identifying a non-healing skin wound in a patient,
   reconstituting the suspension,
   injecting into the patient at a plurality of intradermal sites located about the proximal periphery of the non-healing skin wound the reconstituted suspension, and
   covering an exposed surface of the non-healing wound with a first meshed placental membrane material,
   wherein the first meshed placental membrane is configured to expand greater than three times an up to six times its original area;
   wherein the first meshed placental membrane material comprises a single layer of cuboidal epithelial cells, a basement membrane layer and a stromal layer,
   wherein injecting the suspension into the patient in conjunction with covering the exposed surface of the non-healing wound with the meshed placental membrane material promotes healing of the non-healing skin wound.

6. The method according to claim 5 wherein the plurality of cells derived from amnion are purified or extracted from an intact amniotic membrane.

7. The method according to claim 5 wherein the plurality of cells derived from amnion are derived from a homogenized amniotic membrane.

8. The method according to claim 5 further comprising washing the plurality of amniotic fluid cells and the plurality of cells derived from amnion, and wherein the step of forming a suspension comprises suspending the plurality of amniotic fluid cells and the plurality of cells derived from amnion in an isotonic solution.

9. The method according to claim 5 wherein the cells derived from amnion express electrolytes, growth factors, carbohydrates, lipids, proteins, amino acids, lactate, pyruvate, enzymes and hormones.

10. The method according to claim 5 wherein the suspension includes $1 \times 10^6$ of the plurality of amniotic fluid cells and the plurality of cells derived from amnion per 100 µl of a fluid.

11. The method according to claim 5 wherein the stromal layer of the first meshed placental membrane material is placed in direct contact with the exposed surface.

12. The method according to claim 5 comprising stretching the first meshed placental membrane material to entirely cover the exposed surface.

13. The method according to claim 5 wherein covering the exposed surface of the non-healing wound with the first meshed placental membrane material reduces a rate of passive evaporative water loss from the non-healing wound.

14. The method according to claim 5 wherein openings through the first meshed placental membrane material promote and allow for wound draining and movement of cells through the meshed placental membrane material.

15. The method according to claim 5 wherein the non-healing skin wound is located on one or more of a foot, an arm, a leg and an abdomen of the patient.

16. The method according to claim 5 wherein the first meshed placental membrane material includes a chorion layer.

17. The method according to claim 5 wherein the suspension includes fetal cells.

* * * * *